United States Patent [19]

Patel

[11] Patent Number: 4,719,104

[45] Date of Patent: Jan. 12, 1988

[54] HAIR CONDITIONING COMPOSITION AND METHOD

[75] Inventor: Chaitanya Patel, Hanover Park, Ill.

[73] Assignee: Helene Curtis, Inc., Chicago, Ill.

[21] Appl. No.: 882,026

[22] Filed: Jul. 3, 1986

Related U.S. Application Data

[63] Continuation of Ser. No. 667,740, Nov. 2, 1984, abandoned.

[51] Int. Cl.$^4$ .............. A61K 7/06; A61K 7/09; A61K 7/42
[52] U.S. Cl. .................. 424/70; 424/59; 424/71; 424/72
[58] Field of Search .............................. 424/70

[56] References Cited

U.S. PATENT DOCUMENTS

| | | | |
|---|---|---|---|
| Re. 30,874 | 3/1982 | Dasher et al. | 424/70 |
| 4,465,802 | 8/1984 | Dennen et al. | 424/70 |
| 4,496,536 | 1/1985 | Möller et al. | 424/70 |

FOREIGN PATENT DOCUMENTS

| | | | |
|---|---|---|---|
| 0064433 | 5/1977 | Japan | 424/70 |
| 55-2648 | 1/1980 | Japan | 424/70 |
| 0206605 | 12/1982 | Japan | 424/70 |
| 0002398 | 1/1983 | Japan | 424/70 |
| 7604794 | 11/1976 | Netherlands | 424/70 |

OTHER PUBLICATIONS

Cosmetics & Toiletries, 4/1979, pp. 90 to 93, vol. 94, McCarthy et al.

*Primary Examiner*—Dale R. Ore
*Attorney, Agent, or Firm*—Dressler, Goldsmith, Shore, Sutker & Milnamow, Ltd.

[57] ABSTRACT

A human hair conditioner and methods are disclosed. The conditioner consists essentially of an aqueous composition containing 0.25–4 percent static-reducing agent, 0.05–1.0 percent cationic film-forming polymer that contains a plurality of quaternary nitrogen atoms, and 0.25–4 percent distearyldimethylammonium salt, wherein the weight ratio of the static-reducing agent to the cationic polymer is about 2:1 to about 20:1.

15 Claims, No Drawings

HAIR CONDITIONING COMPOSITION AND METHOD

This application is a continuation, of appliation Ser. No. 667,740, filed Nov. 2, 1984 now abandoned.

DESCRIPTION

1. Technical Field

The present invention relates generally to conditioners for human hair, and more specifically to conditioners and methods of their use that impart a reduced static charge to hair treated with a conditioner containing a cationic polymer when that hair in a dry state is combed, and that improve hair set and style.

2. Background Art

Hair conditioning compositions that contain a quaternary nitrogen compound as the principal conditioning agent are well known in the cosmetic arts. Such conditioning agents may be monomeric, non-polymeric molecules of relatively low molecular weight that contain one or two quaternerized nitrogen atoms along with one $C_{12}$–$C_{18}$ alkyl group or two $C_{12}$–$C_{16}$ alkyl groups per quaternary nitrogen atom.

Human hair normally is anionic and has a net negative charge in aqueous compositions at neutral pH values. The cationic conditioning agents are believed to deposit on hair through a cation-anion interaction.

While relatively low molecular weight conditioning agents can provide adequate conditioning effects such as wet combing and detangling, and can reduce or eliminate the static charge induced in dry hair by combing, they typically leave dry hair limp, having little body, and also reduce the set holding ability of the conditioner-treated hair to less than that shown for similar hair that was not treated with such a conditioner.

Polymeric conditioning agents that contain a plurality of quaternary nitrogen atoms are also well known. One problem long associated with conditioning compositions that contain such polymeric quaternary nitrogen compounds is that the conditioned hair in its dry state; i.e., after conventional drying in the air or with a hair dryer, typically obtains an induced static charge upon combing.

The cause of the combing induced static charge in hair conditioned with quaternary nitrogen-containing polymers is thought to be due to the very high substantivity of such polymers to the hair that makes the previously anionic hair cationic. The presence of a static charge on the hair fibers causes fiber-fiber repulsions that can give the hair an unwanted "fly-away" look.

Polymeric quaternary nitrogen-containing conditioning agents that are film-forming polymers can also provide a degree of set holding to dry, conditioner-treated hair. However, in many cases, the set holding attributes that can be obtained using polymeric conditioners are offset by the detriment of increased static charge on the hair and its resulting "fly-away" look.

It would therefore be beneficial if a quaternary nitrogen-containing hair conditioning composition could be found that reduces the static charge normally associated with combed, dried hair conditioned with a cationic polymer. It would also be beneficial if the set holding properties obtainable from the use of film-forming, polymeric quaternary nitrogen-containing conditioning agents could be taken advantage of without the usually attendant increase in static and "fly away" on combing dry, conditioned hair that such conditioning agents normally provide.

BRIEF SUMMARY OF THE INVENTION

The present invention contemplates a human hair conditioner that provides a reduced static charge to dried, combed, conditioned human hair. That conditioner consists essentially of an aqueous composition of about 0.25 to about 4 weight percent of a static-reducing agent comprised of a nonionic, water insoluble, non-oily organic material that is a liquid at 20° C., having a Brookfield viscosity at 26° C. of less than about 50 centipoises, and a refractive index at 25° C. of about 1.4 to about 1.5 such as the mixed benzoate esters of $C_{12}$–$C_{15}$ alcohols or caprylic/capric triglyceride, about 0.05 to about 1.0 weight percent of a cationic, film-forming polymer containing a plurality of quaternary nitrogen atoms, and about 0.25 to about 4 weight percent of a distearyldimethylammonium salt, the weight ratio of the above static-reducing agent to the cationic polymer being about 2:1 to about 20:1.

In preferred practice, the hair conditioning composition is an aqueous emulsion in which the ingredients are stably dispersed to form a substantially homogeneous composition.

Also contemplated is a method of conditioning human hair in the presence of a hair set-improving cationic polymer to provide a reduced amount of static charge on that hair when the conditioned hair in the dry state is combed. Here, the above-discussed human hair conditioning composition is provided and is applied in a substantially homogeneous form to human hair. Thus, the conditioner itself need not be substantially homogeneous at ambient temperatures, but when it is applied to the hair, it is in a substantially homogeneous form; i.e., the conditioner may separate on standing at room temperature, but may be made substantially homogeneous by agitation, as by shaking immediately prior to use. The applied conditioner is maintained on the hair for a time period sufficient for the conditioner to contact the hair fibers. The contacted hair fibers are thereafter rinsed with water, and the water-rinsed hair is dried.

The composition and method of the present invention provides several benefits and advantages.

One benefit is that hair conditioned with a composition of this invention, when combed in the dry state, has a relatively reduced amount of static charge.

An advantage of the present invention is that a cationic, quaternary nitrogen-containing, film-forming polymer may be used in an amount sufficient to improve the set holding characteristics of conditioned hair without the attendant static charge that is normally found when such polymeric conditioning agents are utilized in an amount to provide set holding.

Another advantage of the present invention is that a minimal amount of non-polymeric, relatively low molecular weight conditioning agent is deposited on the hair, thereby aiding the set holding properties of the conditioned hair, rather than increasing the limpness of the hair.

Still further benefits and advantages of the present invention will be apparent to those skilled in the art from the detailed disclosures and examples that follow.

DETAILED DESCRIPTION OF THE INVENTION

The hair conditioning compositions of this invention are aqueous compositions, and in addition to water consist essentially of particular amounts of each of three ingredients, two of which ingredients are present at a particular weight ratio to each other. Those three ingredients are (a) a salt of the distearyldimethylammonium ion, (b) a cationic, film-forming polymer containing a plurality of quaternary nitrogen atoms and (c) a static-reducing agent that is a nonionic, water-insoluble, non-oily organic material that is a liquid at 20° C., having a Brookfield viscosity at 26° C. of less than about 50 centipoises, and a refractive index at 25° C. of about 1.4 to about 1.5 such as the mixed benzoate esters of $C_{12}$-$C_{15}$ alcohols and the mixed triglyceride reaction product of capric and caprylic acids with glycerol.

The term "distearyldimethylammonium salt" is intended to include the pure or substantially pure named cationic compound, as well as to include materials such as dimethyldi(hydrogenated tallow)ammonium salts that contain about 60 to about 70 weight percent $C_{18}$-alkyl groups in their tallow-derived fatty chains. Thus, the distearyldimethylammonium salt may also be referred to as a dialkyldimethylammonium salt whose two alkyl groups are each predominantly, at least about 60 to about 70 weight percent, composed of chains containing 18 carbon atoms ($C_{18}$-chains).

The distearyldimethylammonium salt provides a conditioning effect to the compositions of this invention, above that provided by the cationic quaternary nitrogen-containing polymer, without substantially impairing the set holding effect of the composition as a whole, as might be expected from a usually used non-polymeric, relatively low molecular weight quaternary nitrogen-containing conditioning agent. As already noted, such usually utilized relatively low molecular weight conditioners (less than 1100 daltons) that contain one or two quaternary nitrogen atoms and one $C_{12}$-$C_{18}$ alkyl groups or two $C_{12}$-$C_{16}$ alkyl groups per quaternary nitrogen typically make treated hair relatively limp, compared to untreated hair, and thereby reduce set holding.

The anion of the distearyldimethylammonium salt may be selected from a wide group of anions. Included in that group are the halides such as fluoride, chloride, bromide, and iodide; monovalent and divalent inorganic anions such as nitrate, nitrite, sulfate, bisulfate, carbonate and bicarbonate; organic carboxylic acids containing up to about 4 carbon atoms such as formate, acetate and fumarate; and organic sulfates and sulfonates containing up to about 8 carbon atoms such as ethyl sulfate, methyl sulfate, benzene sulfonate and toluene sulfonate. Monovalent anions, and the halides, particularly chloride, are especially preferred.

The distearyldimethylammonium salt may be present in the compositions of this invention in an amount of about 0.25 to about 4 weight percent of the total composition. More preferably, the distearyldimethylammonium salt is present in an amount of about 0.5 to about 2.5 weight percent of the total composition.

The distearyldimethylammonium salt appears to be unique among the relatively low molecular weight, monomeric (non-polymeric) quaternary nitrogen-containing materials. Specifically, increasing the amount of this material used as a hair conditioning agent present in a conditioning composition above a predetermined, relatively low amount does not increase the amount of distearyldimethylammonium salt that deposits on the hair. This point is illustrated in Example 2 hereinafter.

In that example, it is shown that at 1.0 weight percent of the composition of the distearyldimethylammonium chloride, used illustratively herein as a distearyldimethylammonium salt, substantially the same amount of cationic conditioning agent is found on the hair in the presence or absence of 2 weight percent caprylic/capric triglyceride. In addition, there is no substantial change in the deposition of the distearyldimethylammonium chloride in the presence of 2 percent caprylic/capric triglyceride when the distearyldimethylammonium chloride is present over a range of 0.5 to 2 weight percent of the composition.

Those results may be compared with the results obtained using the other, usually used conditioning agents illustrated in that Example. It is there shown that a different amount of conditioning agent is deposited on the hair in the absence of caprylic/capric triglyceride from that deposited when the triglyceride is present. It is also shown that increasing amounts of the other quaternary nitrogen-containing compounds are deposited with increasing concentrations of those compounds when the caprylic/capric triglyceride is held at a constant level of 2 weight percent.

The data of Example 2 further illustrate that less of the distearyldimethylammonium salt is deposited on the hair than is deposited by any of the usually used quaternary nitrogen-containing conditioning agents of that Example, when all of the relatively low molecular weight materials are originally present at the same concentration. It is believed that the relatively minimal deposition of the distearyldimethylammonium salt plays a significant role in the improved set holding properties exhibited by hair conditioned using that conditioning agent.

Thus, the use of a conditioning amount of a distearyldimethylammonium salt as disclosed herein in an aqueous medium provides an improved human hair conditioner. An improved conditioner composition may also contain additional cationic hair conditioning agents such as the polymeric materials described herein, and/or the usually used non-polymeric, relatively low molecular weight hair conditioners that contain one or two quaternary nitrogen atoms per molecule and one $C_{12}$-$C_{18}$ alkyl group or two $C_{12}$-$C_{16}$ alkyl groups per molecule. Such multi-cationic component conditioners preferably contain the distearyldimethylammonium salt as the principal hair conditioning agent; i.e., that salt constitutes at least about 60 weight percent relatively of the low molecular weight cationic, quaternary nitrogen-containing conditioning agent present. In any event, an improved human hair conditioner of this invention contains water and a hair-conditioning amount of a cationic, quaternary nitrogen-containing conditioning agent that is a distearyldimethylammonium salt as described herein. Such improved conditioners are utilized to condition hair, and to reduce the hair limpness normally associated with a non-polymeric, cationic conditioning agent, following the methods described herein.

A useful distearyldimethylammonium salt is the distearyldimethylammonium chloride sold under the trademark AROSURF®TA-100 by Sherex Chemical Co, Inc. of Dublin, Ohio. That material is sold as a white powder said by its supplier's literature to typically be 95 percent active and contain 2 percent of the free amine and its hydrochloride salt. The supplier's literature indicates its use to be as a fabric softener for imparting softness and fluffiness to fabrics, and improved antistatic properties for cotton, rayon, nylon and other synthetic fibers.

The supplier's literature also indicates that a possible mechanism for its use as a fabric softener is the material's substantivity to negatively charged surfaces, its ability to exhaust from dilute aqueous dispersions and to "plate out" on those substrates. That literature suggests a typical formulation to contain 15-35 weight percent of the product along with diluent extenders.

A particular composition suggested by the supplier contains 30 weight percent of the quaternary fabric softener and 70 weight percent diluent. The use of 1.5-4 ounces of that dry formulation to 100 pounds dry weight of fabric is recommended.

Using the supplier's latter suggested fabric softener formulations, it may be calculated that the fabric softener is utilized in an amount of from 0.028 to 0.075 percent of the weight of fabric to be softened. Using similar calculations and presuming that one milliliter of a composition of this invention of Example 2 weighs one gram, it is seen that when used herein in an amount of 0.25 to 4 weight percent of a human hair conditioner, distearyldimethylammonium chloride is used at about 0.14 to about 2.2 percent of the weight of hair treated.

Thus, the compositions herein utilize at about 5 up to about 30 times the amount of distearyldimethylammonium chloride that is suggested by the supplier for use as a fabric softener. Use of similar calculations for the more preferred amounts of distearyldimethylammonium chloride used herein, shows its concentration to be about 10 to about 20 times greater than that suggested for fabric softener use.

The amount of distearyldimethylamonium salt utilized herein, about 0.25 to about 4 weight percent, is considered to constitute a dilute aqueous dispersion. Nevertheless, the results of Example 2 and Example 7 indicate that distearyldimethylammonium chloride does not exhaust from the composition as is suggested by the manufacturer as to its use as a fabric softener.

In addition, increasing amounts of this conditioning agent do not cause an increasing amount of deposition as is the case for the other, usual conditioning agents studied. Furthermore, the amount of distearyldimethylammonium salt utilized in the present human hair conditioners is about 5 to about 30 times greater than that suggested for use as a fabric softener. It is still further noted that distearyldimethylammonium salts do not provide softness or fluffiness (limpness) to hair as compared to other, usually used hair conditioners.

It is therefore believed that the use of a distearyldimethylammonium salt as a conditioning ingredient of a human hair conditioner is different from the use of the same material as a fabric softener.

The *CTFA Cosmetic Ingredient Dictionary* (hereinafter referred to as the *CTFA Dictionary*), Third Edition, published by the Cosmetic, Toiletry and Fragrance Association, Inc., Washington, D.C., 1982 names distearyldimethylammonium chloride as distearyldimonium chloride, and lists two other sources of the material. Those sources are American Hoechst Corporation Industrial Chemicals Division, Somerville, N.J., that sells the material under the trademark BENAMIN DSAC, and Humko Chemical Division of Witco Chemical Corporation of Memphis, Tenn., that sells this material under the trademark KEMAMINE Q-9902C. Distearyldimethylammonium chloride from any of the three suppliers may be used herein, preferably with adjustments for the percentage of active material present in the products.

A dimethyldi(hydrogenated tallow)ammonium salt is named in the *CTFA Dictionary* as quaternium-18, and is shown to be available from two sources. These sources are the Sherex Chemical Company, Inc., Dublin, Ohio, a subsidiary of Schering A. G. that sells the material under the trademarks ADOGEN-442, -442-100P and VARISOFT 100, and from Humko Chemical Division of Witco Chemical Corporation that sells this material under the trademark KEMAMINE Q-9702C. A similar material described and shown as bis(hydrogenated tallow alkyl)dimethylammonium methylsulfate is named in the *CTFA Dictionary* as quaternium-18 methosulfate, and is available from Lonza, Inc., Fairlawn, N.J., supplied under the trademark CAROSOFT V-100. Each of the above materials may also be utilized herein, again preferably with adjustments for the percentage of active materials present.

The second ingredient of a composition of this invention is a static-reducing agent. The static-reducing agent is a nonionic organic material that is water-insoluble, non-oily, has a Brookfield viscosity at 26° C. (79° F.) of less than about 50 centipoises, is a liquid at 20° C., and has a refractive index at 25° C. of about 1.4 to about 1.5.

As used herein, the term "nonionic" is meant to indicate that the static-reducing agent bears no ionic charge in an aqueous composition, and therefore is free from cationic groups such as quaternary ammonium groups or protonatable nitrogen atoms, anionic groups such as carboxylic, sulfonic or phosphoric acid functionality, and is also free from zwitterionic functionality such as is found in betaines, sulfobetaines and may be represented in the formulae for amine oxides. The term "water-insoluble" is meant to have its usual implication in the art, namely that the static-reducing agent has substantially no solubility in water at 20° C., inasmuch as every material has some, albeit small, solubility in water. The term "non-oily" is used herein to mean that the static-reducing agent does not provide a greasy, oily feel to the skin when it is applied thereto. These agents have a Brookfield viscosity of less than 50 centipoises when measured at 26° C. (79° F.), and may therefore be referred to as having a low viscosity. The static-reducing agents useful in here are liquids at 20° C.

A further characteristic of the static-reducing agents is that they have refractive indices at 25° C. of about 1.4 to about 1.5. In addition to lowering the static charge on dry, combed hair conditioned with a cationic polymer-containing human hair conditioner, the static-reducing agent also deposits to some extent on the hair fibers. Since this material deposits on the hair, it is important that the deposit not make the hair appear to be dull. Consequently, a relatively high refractive index coupled to the ability to reduce static charge induced on combing hair treated with a cationic polymer and the before-mentioned properties is an important, additional characteristic of the static-reducing agent.

Two static-reducing agents have been found to be particularly useful. These materials are both esters.

One, which is particularly preferred, is the reaction product of a mixture of caprylic and capric acids with glycerol; i.e., a glycerol mixed $C_8$-$C_{10}$ fatty acid triester. This material is available commercially under the trademarks LEXOL GT 865 and 855 from Inolex Chemicals, Philadelphia, Pa. Similar materials are sold under the trademarks MYRITOL 318 and STANDAMUL 318 both supplied by the Chemical Specialty division of the Henkel Corporation of Hoboken, N.J., LIPONATE GC supplied by LIPO Chemicals, Inc., Paterson, N.J., MIGLYOL-810 Neutral oil and -812 Neutral oil supplied by Dynamit Nobel AG (Kay-Fries, Inc. distributor), and Vegetable Oil 1400, NEOBEE M-5 and NEOBEE O supplied by PVO International, Inc., New York, N.Y.

All of these materials are designated in the *CTFA Dictionary* as caprylic/capric triglyceride, and will be so denominated herein. Typical physical properties for caprylic/capric triglyceride include a saponification value of about 335–355, an acid value of 0.1 maximum, an iodine value of 0.5 to 1.0 maximum, solidification point of about −8° C. or less, a specific gravity at 25° C. of 0.945–0.95, and a refractive index at 25° C. of about 1.43 to about 1.45.

The suppliers' literature for caprylic/capric triglyceride suggest its use as an emollient in creams and lotions, as a vehicle for bath oils and electric pre-shave lotions and as a vehicle for medicinals, antibiotics and vitamins. Uses as a stabilizer for emulsions and in cosmetic waxes are also suggested.

The second useful static-reducing agent is an ester reaction product of mixed $C_{12}$–$C_{15}$ alcohols and benzoic acid. This material has the *CTFA Dictionary* designation C12-15 alcohols benzoate and is commercially available under the trademark FINSOLV TN sold by Finetex, Inc. of Elmwood Park, N.J. This material is noted in U.S. Pat. Nos. 4,275,222; 4,278,655, 4,293,544, 4,322,545 and 4,323,694 whose disclosures are incorporated herein by reference.

Typical physical properties for C12-15 alcohols benzoate from the supplier's literature include a boiling point of 300° C., a freezing point range of −3° to −12° C., a specific gravity of 0.923, a refractive index of 1.479–1.481, a Brookfield viscosity at 70° F., RV1 spindle and 100 rpm of 40–45 centipoises, and a saponification value of 170–177.

The supplier's literature describes FINSOLV TN as a non-oily skin lubricant, as well as an emollient for use in body oils, bath oils and skin creams without the oily feel of mineral oil or isopropyl myristate, the latter material also being said to be replaceable by FINSOLV TN. FINSOLV TN is also said to be suited especially for imparting a dry talc feel to the above compositions as well as to conditioning shampoos and hair conditioners.

The static-reducing agent is present in about 0.25 to about 4 weight percent of the conditioning composition, and is more preferably present at about 1.5 to about 2.5 weight percent.

As is shown from the data in Examples 5 and 8, the static-reducing agent, when admixed in the above amounts and in the weight ratios to the cationic film-forming polymer, discussed hereinafter, interacts with that polymer to reduce the static charge induced by combing dried hair treated with the conditioner that also includes a useful amount of a distearyldimethylammonium salt. The combing-induced static is reduced to a level below that induced by a similar composition that is free of the static-reducing agent.

For bleached-waved hair, the induced static charge on the hair may be further reduced to a level below that induced when either the polymer or the static-reducing agent is used alone in the absence of the other ingredient. These results are quite unexpected and the reasons for them are not understood.

The third ingredient of a composition of this invention is a cationic, film-forming polymer having a plurality of quaternary nitrogen atoms; i.e., a polymeric quaternary nitrogen-containing conditioning agent. The quaternary nitrogen atoms of such polymers preferably bear at least two methyl substituents.

The useful polymers are "cationic" in that they bear a net positive ionic charge in aqueous solution. The term "film-forming" is meant to indicate that the polymers provide a film when a polymer-containing aqueous solution or dispersion is spread over a substrate and allowed to dry. Quaternary nitrogen atoms of these polymers are each covalently bonded to four carbon atoms and are therefore positively charged and cationic, since the usual valence for nitrogen is three.

Illustrative cationic, film-forming polymers include (a) the materials sold under the trademarks POLYMER JR-30M, JR-125 and JR-400 by Union Carbide Corp., Danbury, Conn., that are designated in the *CTFA Dictionary* as polyquaternium-10 and said to be a polymeric quaternary ammonium salt reaction product of hydroxyethyl cellulose reacted with a trimethylammonium-substituted epoxide, and are disclosed and claimed in U.S. Pat. No. 3,472,840, whose disclosures are incorporated herein by reference; (b) the material sold under the trademarks CELQUAT H60 and L200 by National Starch and Chemical Corp., Bridgewater, N.J., that are designated in the *CTFA Dictionary* as polyquaternium-4, and said to be copolymers of hydroxyethyl cellulose and diallyldimethylammonium chloride, the supplier's literature indicating that the cationic polymer is grafted onto the cellulosic backbone; (c) and (d) the materials sold under the trademarks MERQUAT-100 and -550 (and a material very similar in description to MERQUAT-550 designated MERQUAT-S) by the Merck Chemical Division of Merck & Co., Inc., Rahway, N.J., that are designated as polyquaternium-6 and -7 in the *CTFA Dictionary*, and are said to be a homopolymer of diallyldimethylammonium chloride and a copolymer reaction product of diallyldimethylammonium chloride and acrylamide monomers, respectively; (e) the materials sold under the trademarks GAFQUAT-734 and -755 by GAF Corp., Wayne, N.J., that are designated as polyquaternium-11 in the *CTFA Dictionary* and are said to be quaternary ammonium polymer reaction products of dimethyl sulfate and a copolymer of vinyl pyrrolidone and dimethylaminoethyl methacrylate; (f) the material sold under the trademark BINA ® QAT P-100 by Ciba-Geigy Corporation Dyestuff & Chemicals Division, of Greensboro, N.C., that is said by the supplier to have the CTFA adopted name polyquaternium-15, to be a copolymer of acrylamide and methacryloyloxyethyl trimethylammonium chloride and to have a degree of quaternization of 2.2 millimoles per gram of polymer; and (g) the material sold under the trademarks LUVIQUAT FC-905, -550 and -37 by BASF Aktiengesellschaft, Ludwidshafan, FRD (also available from ARMAC Industrial Chemicals Division, Philadelphia, Pa.), that are said in the supplier's literature to be copolymers of methylvinylimidazolium chloride and vinyl pyrrolidone, the copolymers being prepared from the monomers in weight ratios of 95:5, 50:50 and 30:70, respectively. The cationic, film-forming polymer sold under the trademark POLYMER JR-30M, polyquaternium-10, is particularly preferred.

Each of the above cationic polymers is suggested by its supplier or known by those skilled in the art to be useful as a hair conditioning agent. Each is also known or suggested to have film-forming properties and is thereby possibly useful for improving the set holding properties of a human hair conditioner. However, each of the above materials, when used in an amount sufficient to provide a desired amount of set holding and conditioning, is also so substantive to the hair that the normally anionic hair becomes cationic and is susceptible of bearing a static charge when combed in the dry state. The preferred combination of ingredients herein provides desirable levels of conditioning and set holding, while minimizing combing-induced static that would otherwise be present due to the use of a cationic polymer.

The quaternary nitrogen-containing, film-forming polymer may be present in an amount in about 0.05 to about 1.0 weight percent of the total composition, and is more preferably present at about 0.1 to about 0.5 weight percent of the composition.

The weight ratio of the static-reducing agent to the cationic, quaternary nitrogen-containing polymer is also of import herein. That weight ratio is preferably about 2:1 to about 20:1. In more preferred practice, that weight ratio is about 5:1 to about 20:1.

As was noted previously, use of the static-reducing agent in the conditioning composition containing the cationic polymer provides conditioned hair with less induced static charge on combing the dry hair than does a similar composition that is free from the static-reducing agent. The data of Example 5 illustrate the effect on combing-induced static charge provided by the cationic polymer, and the beneficial effect of the static-reducing agent in decreasing the induced static when used in the various proportions by weight disclosed above.

The data in Example 8 illustrate the effect on combing-induced static provided individually by the cationic polymer and static-reducing agent, as well as their synergistic effect when used together in the various proportions by weight disclosed above.

The conditioning compositions of this invention are substantially homogeneous when applied to the hair. In preferred practice, the composition is a stable, non-settling, non-separating aqueous emulsion; i.e., an emulsion from which components neither precipitate nor separate into different phases upon standing at a temperature of about 20° C. (about 68° F.) for a period of at least one month.

Thus, the composition may contain one or more emulsifying agents that provide the above-described stable emulsion while not materially affecting the basic and novel characteristics of the composition such as compromising the desired effect of providing lessened static to conditioned hair than is otherwise provided by a composition of this invention.

Exemplary emulsifying and thickening agents useful herein include cetyl and stearyl alcohols and mixtures thereof; polyoxyethylene glycol ethers of $C_{14}$–$C_{18}$ alcohols that contain an average of about 1 to about 7 polymerized ethylene oxide units per molecule and their mixtures such as the materials denominated pareth-45-7, ceteth-1, ceteth-5, oleth-3, steareth-2 and steareth-6 in the *CTFA Dictionary*; and polyoxypropylene $C_{12}$–$C_{18}$ alcohol ethers containing an average of about 10 to about 30 polymerized propylene oxide units per molecule and their mixtures such as the materials denominated PPG-11 stearyl ether, PPG-15 stearyl ether, PPG-30 cetyl ether and PPG-23 oleyl ether in the *CTFA Dictionary*. Nonionic hydroxyalkylcellulose ether derivatives such as hydroxyethylcellulose and hydroxypropylmethylcellulose and the like, as are well known in the art as useful thickeners.

As already noted, the compositions of this invention need be substantially homogeneous only at the time they are applied to the hair fibers, and consequently their presence in a stable, non-settling, non-separating emulsion, while preferred, is not required. It is also noted that the static-reducing agent is water-insoluble.

A simple composition may also be prepared in which the static-reducing agent, when present, is made dispersible, and the dispersion of the distearyldimethylammonium salt is improved by use of a cosmetically acceptable organic, water-miscible solvent such as propylene glycol, ethanol, glycerol and the like, as are known to those skilled in the art. For example, a useful composition may be prepared that contains water, having dispersed therein 2 percent by weight propylene glycol, 2 percent by weight caprylic/capric triglyceride, 0.5 to 2 percent by weight distearyldimethylammonium chloride and 0.15 weight percent polyquaternium-10. Similar compositions containing about 5 weight percent ethanol are also useful. Additional compositions containing about 2 weight percent propylene glycol or about 5 weight percent ethanol and about 0.25 to about 4 weight percent of a distearyldimethylammonium salt may also be prepared and utilized herein. Such compositions may be made substantially homogeneous by agitation as by shaking immediately prior to use to form compositions that may then be applied to the hair.

In addition to emulsifying agents, other ingredients that do not affect the basic and novel static-lowering effects of a composition of this invention may also be included. Exemplary of such materials are viscosity controlling salts such as alkali metal or ammonium halides including sodium chloride, potassium chloride, ammonium bromide, and the like; pH value adjusting agents such as hydrochloric acid, citric acid, sodium hydroxide, and the like; preservatives, colorants and sun-screening, ultraviolet light-absorbing agents as are known in the art.

Also contemplated by this invention is a method of conditioning human hair. This method includes the steps of providing a human hair conditioner (a) that is the improved hair conditioner containing water and a conditioning amount of a distearyldimethylammonium salt, or (b) for conditioning in the presence of a hair set-improving cationic polymer to provide a reduced amount of combing-induced static charge to the hair when that conditioned hair in the dry state is combed consists essentially of an aqueous composition of about 0.25 to about 4 weight percent of a static-reducing agent described before, about 0.05 to about 1.0 weight percent of a quaternary nitrogen-containing conditioning film-forming polymer and about 0.25 to about 4 weight percent of a distearyldimethylammonium salt; the weight ratio of the static-reducing agent to the quaternary nitrogen-containing polymer of such a composition is about 2:1 to about 20:1.

The conditioning composition so provided is applied in a substantially homogeneous form, preferably as a stable emulsion, to human hair. The applied conditioner is maintained on the hair for a time period sufficient for the conditioner to contact the hair fibers. Preferably, the conditioner is physically spread through the hair with the fingers or by a comb or other means to assure that contact. The contacted hair fibers are then rinsed with water, and the water-rinsed, conditioned hair is dried.

Hair treated according to this method has less combing-induced static when it is combed in a dried state than does hair treated with a similar composition that is free of the static-reducing agent. In addition, use of the above method also typically provides an improved set to freshly shampooed chemically treated hair such as hair that has been bleached and/or waved as compared to other conditioners known in the art, particularly those other conditioners that provide similar conditioning and low induced static charge effects.

The invention is further illustrated by the examples that follow.

BEST MODES FOR CARRYING OUT THE INVENTION

EXAMPLE 1. Hair Conditioning Compositions

This example describes the preparation of hair conditioning compositions of this invention containing a static-reducing agent in combination with a cationic, film-forming polymer having a plurality of quarternary nitrogen atoms, and a distearyldimethylammonium salt. The ingredients and their amounts are listed in the Table below, followed by a method of preparation for the compositions.

| Ingredient | A | B | C | D | E |
|---|---|---|---|---|---|
| Oil Phase I | | | | | |
| Distearyldimethylammonium chloride | 0.5 | 1.0 | 1.5 | 2.0 | 2.0 |
| Static-reducing agent A* | 0.5 | — | 1.0 | — | 2.0 |
| Static-reducing agent B** | — | 0.5 | — | 1.5 | — |
| Stearyl alcohol | 1.0 | 2.0 | 2.0 | 2.0 | 2.0 |
| Polyoxyethylene (2) stearylether | 1.0 | 1.0 | 1.0 | 1.0 | 1.0 |
| Polyoxypropylene (30) cetylether | 0.5 | 0.5 | 0.5 | 0.5 | 0.5 |
| Ultraviolet absorber | q.s. | q.s. | q.s. | q.s. | q.s. |
| Waterphase II | | | | | |
| Hydroxyethylcellulose | 0.25 | 0.25 | 0.5 | 0.5 | 0.50 |
| Quaternary nitrogen-containing polymer*** | 0.10 | 0.10 | 0.05 | 0.30 | 0.15 |
| Preservative | 0.05 | 0.05 | 0.05 | 0.05 | 0.05 |
| Citric acid (50% in water) to pH 4–5 | q.s. | q.s. | q.s. | q.s. | q.s. |
| Sodium hydroxide (25% in water) to pH 4–5 | q.s. | q.s. | q.s. | q.s. | q.s. |
| Potassium chloride | 0.05 | 0.05 | 0.05 | 0.05 | 0.05 |
| Water, soft to 100% | q.s. | q.s. | q.s. | q.s. | q.s. |
| Phase III | | | | | |
| Fragrance | q.s. | q.s. | q.s. | q.s. | q.s. |
| Color | q.s. | q.s. | q.s. | q.s. | q.s. |

*A caprylic/capric triglyceride such as the mixed triester of glycerin and caprylic and capric acids supplied by Inolex Chemicals under the trademark LEXOL GT865.
**A C12-15 alcohols benzoate such as the ester of benzoic acid and $C_{12}-C_{15}$ alcohols supplied by Finetex Inc. under the trademark FINSOLV TN.
***A polymeric quaternary ammonium salt of hydroxyethyl cellulose reacted with a trimethylammonium-substituted epoxide supplied by Union Carbide Corporation under the trademark POLYMER JR-30M.

The compositions are prepared by methods well known in the art for preparing emulsions. Briefly, the ingredients of the oil phase I are heated together in a first vessel to a temperature of about 80°–85° C. (about 175°–185° F.). The ingredients of the water phase II are heated together in a second vessel to a temperature of about 77°–80° C. (about 170°–175° F.). The contents of the second vessel are then added to the heated contents of the first vessel with mixing agitation until a substantially homogeneous emulsion is formed. The emulsion is cooled to about 35° C. (about 95° F.), and the ingredients of phase III are added and admixed to substantial homogeneity.

EXAMPLE 2. Cationic Deposition on Hair

This example demonstrates the beneficial effects of the use of a distearyldimethylammonium salt in human hair conditioner compositions of this invention in depositing cationic material on the hair without resulting in excess deposition of the cationic conditioning agent on the hair.

Natural white microtresses of human hair (DeMeo Brothers, New York), of approximately 4 inches in length and about 0.1 grams in weight were embedded in standard size tresses of about 6 inches in length and about 1.75 grams in weight to form composite tresses. Each composite tress was washed with a conventional commercial shampoo in a conventional manner, and excess water was stripped from the hair with the fingers.

The stripped composite tresses were subsequently individually conditioned by applying 1.0 milliliters (ml) of an aqueous conditioner composition containing 2 weight percent propylene glycol, 2 weight percent caprylic/capric triglyceride (static-reducing agent A of Example 1) and a quaternary ammonium compound of the type and amount shown hereinafter.

The conditioner composition was rubbed through the composite tresses for one minute after which the tresses were rinsed with a spray of warm water of about 30 degrees C. (about 86 degrees F.) for about 30 seconds. The embedded microtresses were subsequently removed from the treated tresses and were further treated by the well known rubine dye test in the following manner.

Microtresses were individually immersed for a period of about 5 minutes in aqueous solutions containing 0.5 percent rubine dye, having a pH value of 3.5 and a temperature of about 40 degrees C. (about 104 degrees F.). The microtresses were subsequently rinsed with water having a temperature of about 25 degrees C. (about 77 degrees F.) for about 15 seconds. The color of the treated tresses was compared to a color intensity standard ranging from 1 (very faint pink color) to 5 (deep purplish red).

Four cationic materials were examined ranging in amounts of from 0.5 to 2.0 weight percent in the presence and absence of the caprylic/capric triglyceride static-reducing agent. Color intensity standards were separately prepared for each cationic material in the absence of a static-reducing agent. The color intensity standard for each cationic material was prepared by applying a known amount of the cationic material free from the static-reducing agent to a clean dry microtress. The cationic material was rubbed into the hair until it was completely absorbed and the to dry. Each treated microtress was subsequently treated with the rubine dye solution in the manner described above. The color standard microtresses prepared were treated with amounts of individual cationic materials ranging from 0.3 to 2.5 milligrams of cationic material per gram of hair (mg/g).

Panelists were asked to score tresses treated with the conditioner compositions containing the four non-polymeric, relatively low molecular weight, cationic materials against the specific color intensity standard for the cationic material present, and the scores were converted to a calculated, predetermined amount of cationic present per gram of hair.

For comparison, a conditioner composition containing 1 percent cationic material and no static-reducing agent was utilized as a control. The results were as follows, based on duplicate tresses ranked by six panelists.

| Cationic material with 2% static-reducing agent | Weight Percent of composition | Cationic Deposition (mg/g hair) ± S.D.* |
|---|---|---|
| A. Stearyldimethyl benzylammonium chloride | 0.5 | 0.7340 ± 0.1538 |
| | 1.0 | 0.6318 ± 0.1669 |
| | 1.5 | 0.6619 ± 0.2077 |
| | 2.0 | 1.0033 ± 0.2286 |
| B. Cetyltrimethyl- ammonium chloride | 0.5 | 0.5404 ± 0.0294 |
| | 1.0 | 0.5417 ± 0.0347 |
| | 1.5 | 0.7801 ± 0.1515 |
| | 2.0 | 0.7369 ± 0.1316 |
| C. Dicetyldimonium chloride** | 0.5 | 0.9196 ± 0.2737 |
| | 1.0 | 1.1181 ± 0.3171 |
| | 1.5 | 1.3358 ± 0.1955 |
| | 2.0 | 1.5275 ± 0.5580 |
| D. Distearyldimethyl ammonium chloride | 0.5 | 0.5306 ± 0.0365 |
| | 1.0 | 0.5276 ± 0.0445 |
| | 1.5 | 0.5625 ± 0.0549 |
| | 2.0 | 0.5500 ± 0.0280 |

| Cationic material without static-reducing agent | Weight Percent of composition | Cationic Deposition (mg/g hair) ± S.D. |
|---|---|---|
| A. (Above) | 1.0 | 0.8787 ± 0.1973 |
| B. (Above) | 1.0 | 0.6195 ± 0.0630 |
| C. (Above)** | 1.0 | 0.7854 ± 0.2132 |
| D. (Above) | 1.0 | 0.5620 ± 0.0387 |

*S.D. = Standard Deviation.
**CTFA adopted name for a 1-hexadecanaminium, N—hexadecyl-N,N—dimethyl chloride, as defined in the CTFA Dictionary.

The above data show that conditioner compositions containing distearyldimethylammonium chloride produced the least amount of cationic deposition on the hair, and that that amount was substantially the same between a range of from 0.5 to 2.0 weight percent cationic material present in the composition studied, in the presence or absence of a static-reducing agent. The results further show that, except for the composition containing dicetyldimonium chloride, compositions containing the static-reducing agent produced less cationic deposition on the hair than did the corresponding composition without the static-reducing agent.

EXAMPLE 3. Improved Set Retention of Waved Hair

This example demonstrates benefits in improving the set retention of permanently waved hair that has had its curl relaxed by being subjected to multiple washing and conditioning treatments prior to being conditioned with a composition of this invention.

A series of 16 tresses of about 6 inches in length and about 2 grams in weight were prepared from normal, naturally brown human hair (DeMeo Brothers, New York). Each tress was given a permanent wave treatment using a commercial permanent wave salon product for "normal" type hair according to the manufacturer's instructions. The waved tresses were dried for 15 minutes under a commercial salon-style hair dryer set at a "normal" heat setting having an air temperature of about 31 degrees C. (about 89 degrees F.). The dry tresses were suspended vertically, and the curl was allowed to relax naturally at ambient room temperature and humidity for 48 hours.

Sets of four tresses were subjected to a regimen of washing and conditioning with commercially paired shampoo and conditioner products according to the manufacturers' instructions. The regimen for washing and conditioning the hair is described below.

The hair washing procedure comprised the steps of wetting the hair with water, applying 1 ml of shampoo per tress, rubbing and massaging-in the shampoo for about 1 minute, and then spray rinsing the hair with warm water (30 degrees C., about 86 degrees F.) for 1 minute at a flow rate of about 1800 ml per minute. The excess water was removed by stripping the hair with the fingers.

The hair conditioning procedure comprised the steps of applying 1 ml of conditioner product per tress, rubbing and massaging-in the conditioner for about 1 minute, and then spray rinsing the hair with warm water in the manner described above for a period of 30 seconds. Excess water was removed from the hair by sripping it from the hair with the fingers. The tress was dried under a salon-style hair dryer set at a "normal" heat setting as described above for a period of about 15 minutes. The dry, treated tress was then combed with 5 passes of a hard rubber comb.

One total treatment regimen comprised the above steps of hair washing and hair conditioning. Each regimen was repeated in its entirety for a total of 9 treatments. A 10th washing and conditioning regimen was carried out in the same manner, except that the wet, shampooed hair was wound onto a conventional plastic hair roller having an outside diameter of about 0.5 inches (about 1.2 centimeters), and was allowed to dry so wound overnight at ambient room temperature of about 20°–22° C. (about 68–72 degrees F.) at ambient room humidity conditions.

The set holding retention of the 10-times treated tress was examined in the following manner. The dry-wound tress was equilibrated in a chamber for one hour at a relative humidity of 85–90% at an ambient temperature of about 20–22 degrees C. (about 68–72 degrees F.) the tress was removed from the chamber, and the roller was removed from the hair. The unwound tress was suspended vertically, and the hanging length of the curl was measured (initial length). The hanging length of the tress was remeasured at hourly intervals over a period of 6 hours. The amount of set retained by the hair after relaxing the curl for a certain amount of time was calculated from the following formula in a manner well known in the art.

$$\% \text{ Set Retention} = \frac{L - L(t)}{L - L(o)} \times 100,$$

where
L = length of the hair tress fully extended;
L(o) = initial length of the hair curl; and
L(t) = length of the hair curl at time (t).

The percent set retention was plotted against time using a least squares analysis approach described by Diaz and Wong, in "Set Relaxation of Human Hair," *J. Soc. Cosmet. Chem.*, 34, pages 205–212, (1983), which description is incorporated herein by reference. The holding power was calculated from the average area under the curve obtained as a holding power function according to the method of Diaz and Wong.

After the set retention was measured for the 10-times treated tresses, the same tresses received an 11th washing with shampoo as described above, followed by a conditioning treatment with conditioner composition D of Example 1 instead of the commercial conditioner previously used. Set retention was otherwise examined and the holding power function for each tress was calculated in the manner described before.

The set retention obtained after the 10th treatment was compared against that of the 11th treatment by statistically comparing the individual holding power functions calculated from the curves for each treatment. The results are shown below.

| Tress treatment regimen | Holding Power Function (calculated area from % set retention vs. time in hours) | | Percent increase of II-I |
|---|---|---|---|
| | I after 10th Treatment | II after 11th Treatment | |
| 1. Commercial Shampoo A Commercial Conditioner A | 534.4 | | |
| 2. Commercial Shampoo A Conditioner D, Example 1 | | 575.1 | 5 |
| 3. Commercial Shampoo B, Commercial Conditioner B | 544.0 | | |
| 4. Commercial Shampoo B, conditioner D, Example 1 | | 577.5 | 5 |
| 5. Commercial Shampoo C, Commercial Conditioner C | 530.5 | | |
| 6. Commercial Shampoo C, Conditioner D, Example 1 | | 558.4 | 5 |
| 7. Commercial Shampoo D, Commercial Conditioner D | 507.0 | | |
| 8. Commercial Shampoo D, Conditioner D, Example 1 | | 555.3 | 10 |

The above data show that a conditioner of this invention (conditioner D, of Example 1) improved the holding power of each of the waved tresses by a factor of from about 5 to about 10 percent. The improvement was determined to be statistically significant at a confidence level of 95% based on the well known Student's t-test for the tress series #2, #4, and #8 receiving a regimen of treatment with commercial shampoo and conditioner products A, B, and D respectively.

The active conditioner(s) present according to the labeled ingredients in commercial conditioner products were as follows: product A contained dicetyldimethylammonium chloride (previously identified in Example 2); product B contained a mixture of dicetyldimethylammonium chloride and cetyltrimethylammonium chloride; product C contained cetyltrimethylammonium chloride; and product D contained dicetyldimethylammonium chloride.

The results show the beneficial conditioning effect of the conditioner of this invention reflected as an improvement in the holding power of waved hair after multiple washings. The holding power of waved hair is known to be weakened by such multiple washings. Thus, an advantageous boost in the holding power of waved hair over a period of time from a conditioning treatment would be highly beneficial to the lastingness of the curl obtained with permanent wave treatments.

EXAMPLE 4. Improved Set Retention of Waved Hair

The procedure of Example 3 was followed except that the total number of the treatments was doubled. Thus, the holding power function was calculated from the average area obtained from percent set retention versus time in hours curves after a 20th treatment in Column I and a 21st treatment in Column II in the Table below.

| Tress treatment regimen | Holding Power Function (calculated area from % set retention vs. time in hours) | | Percent increase of II-I |
|---|---|---|---|
| | I after 20th Treatment | II after 21st Treatment | |
| 1. Commercial Shampoo A Commercial Conditioner A | 550.6 | | |
| 2. Commercial Shampoo A Conditioner D, Example 1 | | 575.1 | 4 |
| 3. Commercial Shampoo B, Commercial Conditioner B | 549.1 | | |
| 4. Commercial Shampoo B, conditioner D, Example 1 | | 571.2 | 4 |
| 5. Commercial Shampoo C, Commercial Conditioner C | 545.8 | | |
| 6. Commercial Shampoo C, Conditioner D, Example 1 | | 572.5 | 4 |
| 7. Commercial Shampoo D, Commercial Conditioner D | 547.3 | | |
| 8. Commercial Shampoo D, Conditioner D, Example 1 | 583.0 | | 7 |

The data above show that Conditioner D of Example 1 improved the holding power of each of the waved tresses by a factor of from about 4 to about 7 percent. The improvement was determined to be statistically significant at a confidence level of 90% for the tress series #2 and #8, and at a confidence level of 80% for tress series #6 based on a Student's t-test analysis.

It is also noted that the data of Example 3 and of this Example show no reversals of improvement in set holding even though all of the results were not statistically significant at high levels of confidence. The fact that there are no improvement reversals is believed to indicate that the lack of statistically significant differences at high confidence levels is a function of the relatively small number of tresses utilized in each condition, to the relatively wide scatter of data obtained using human hair as a substrate, and to curl relaxation as a method of analysis. It is thus believed that the differences in set holding between the treatment regimens are real, and that the conditioning compositions of the present invention provide improved set holding effects over other conditioners of the art.

EXAMPLE 5. Static Charge Reduction

This example demonstrates the beneficial effect of the static reducing agent used in a hair conditioner of this invention to minimize the static charge induced by cationic polymers when the conditioned, dry hair is combed.

A series of natural brown hair tresses (DeMeo Brothers, New York) about 6 inches in length and about 2 grams in weight were prepared. The tresses were thoroughly washed in the usual manner with a commercial shampoo product known to contain no cationic film-forming polymer containing a plurality of quaternary nitrogen atoms. Excess water was stripped from the hair with the fingers.

The shampooed tresses were individually conditioned with a conditioning solution identified hereinafter by applying 0.5 grams of solution per tress, and permitting the conditioner to maintain contact with the hair fibers for about 30 seconds. Each treated tress was subsequently rinsed for about 30 seconds with tap water having a temperature of about 38 degrees C. (about 100 degrees F.). Each conditioned tress was towel-dried, and then further dried with a conventional electric hair dryer.

Each dried tress was combed to remove any knots. It was then placed in a constant humidity chamber at a relative humidity of about 43% for a period of 24 hours at ambient, room temperature. Static charge was induced on the equilibrated hair and measured as follows.

The equilibrated, treated hair tress was combed with 50 strokes of a hard rubber comb mounted on a motorized device. The electric field strength of the combing-induced static charge on the hair was immediately thereafter measured by the electrostatic field detected with a sensing probe placed at a distance of about 5 inches (about 12 centimeters) from the surface of the tress. The electrostatic field measurement was carried out using a Model 354A ESD monitor supplied by Trek, Inc. having a measuring range of from 0 to 100 kilovolts/meter (kv/m). An average of two readings per conditioning treatment examined was taken.

The conditioning solutions contained 5 weight percent ethanol; 0.05–0.5 weight percent cationic polymer having a plurality of quaternary nitrogen atoms; 0.0–4.0 weight percent of a static-reducing agent; and soft water in quantity sufficient to provide 100 weight percent. Three cationic polymers and two static-reducing agents were examined as identified below.

Static-Reducing Agents

A. Caprylic/capric triglyceride supplied under the trademark LEXOL GT 865 by Inolex Chemicals.
B. C12-C15 Alcohols benzoate supplied under the trademark FINSOLV TN by Finetex Inc.

Cationic Polymers

A. A polymeric quaternary ammonium salt of hydroxyethyl cellulose reacted with a trimethyl ammonium-substituted epoxide supplied under the trademark POLYMER JR-30M by the Union Carbide Corp.
B. A copolymer of hydroxyethylcellulose and diallyldimethylammonium chloride supplied under the trademark CELQUAT L200 by National Starch and Chemical Corp.
C. A copolymer reaction product of diallyldimethylammonium chloride and acrylamide monomers supplied under the trademark MERQUAT 550 by the Merck Chemical Division of Merck & Co.

| Series I Weight Percent Static Reducing Agent A | kv/m Static Charge Measured Weight Percent Cationic Polymer A | | | | | |
|---|---|---|---|---|---|---|
| | 0.05 | 0.1 | 0.2 | 0.3 | 0.4 | 0.5 |
| 0.0 | 60 | 74 | 88 | 105 | 110 | 120 |
| 0.5 | — | — | 77 | — | — | 97 |
| 1.0 | 47 | 59 | 66 | 79 | 86 | 95 |
| 2.0 | — | 53 | — | 78 | — | 91 |
| 4.0 | — | — | 60 | — | — | 89 |

| Series II Weight Percent Static Reducing Agent B | kv/m Static Charge Measured Weight Percent Cationic Polymer A | | | | | |
|---|---|---|---|---|---|---|
| | 0.05 | 0.1 | 0.2 | 0.3 | 0.4 | 0.5 |
| 0.0 | 60 | 74 | 88 | 105 | 110 | 120 |
| 1.0 | 52 | 74 | 78 | 85 | 85 | 86 |
| 2.0 | — | 68 | — | 76 | — | 78 |

| Series III Weight Percent Static Reducing Agent A | kv/m Static Charge Measured Weight Percent Cationic Polymer B | | | | | |
|---|---|---|---|---|---|---|
| | 0.05 | 0.1 | 0.2 | 0.3 | 0.4 | 0.5 |
| 0.0 | 70 | 75 | 78 | 86 | 90 | 98 |
| 0.5 | — | — | 66 | — | — | 82 |
| 1.0 | 41 | 52 | 60 | 70 | 74 | 80 |
| 2.0 | — | 49 | — | 66 | — | 74 |
| 4.0 | — | — | 51 | — | — | 69 |

| Series IV Weight Percent Static Reducing Agent B | kv/m Static Charge Measured Weight Percent Cationic Polymer B | | | | | |
|---|---|---|---|---|---|---|
| | 0.05 | 0.1 | 0.2 | 0.3 | 0.4 | 0.5 |
| 0.0 | 70 | 75 | 78 | 86 | 90 | 98 |
| 1.0 | 67 | 68 | 75 | 83 | 84 | 89 |
| 2.0 | — | 62 | — | 76 | — | 85 |

| Series V Weight Percent Static Reducing Agent A | kv/m Static Charge Measured Weight Percent Cationic Polymer C | | | | | |
|---|---|---|---|---|---|---|
| | 0.05 | 0.1 | 0.2 | 0.3 | 0.4 | 0.5 |
| 0.0 | 39 | 42 | 48 | 52 | 55 | 55 |
| 0.5 | — | — | 48 | — | — | 48 |
| 1.0 | 26 | 30 | 36 | 43 | 47 | 53 |
| 2.0 | — | 28 | 34 | — | — | 49 |
| 4.0 | — | — | 23 | — | — | 29 |

| Series VI Weight Percent Static Reducing Agent B | kv/m Static Charge Measured Weight Percent Cationic Polymer C | | | | | |
|---|---|---|---|---|---|---|
| | 0.05 | 0.1 | 0.2 | 0.3 | 0.4 | 0.5 |
| 0.0 | 39 | 42 | 48 | 52 | 55 | 55 |
| 1.0 | 22 | 23 | 25 | 31 | 35 | 42 |
| 2.0 | — | 21 | — | 25 | — | 37 |

The above data show that combing-induced static charge on the hair increased as the amount of cationic polymer increased, even in the presence of the static-reducing agent. The data also show, however, that the static-reducing agent decreased the static charge on the hair induced by the cationic polymer below levels induced by a similar composition free of the static-reducing agent.

EXAMPLE 6. Cationic Deposition on Hair

The procedure of Example 2 was carried out, except that the aqueous conditioning composition contained 2 weight percent propylene glycol, 2 weight percent distearyldimethylammonium chloride and from 0.5 to 3.0 weight percent of static-reducing agent as shown below.

The amount of cationic deposition on the hair was calculated from panelist ratings based on the specific cationic color standards for distearyldimethylammonium chloride, as discussed in Example 2. The results are shown below.

| Static reducing Agent (SRA) | Weight percent of SRA | Cationic Deposition (mg/g hair) ± S.D. |
|---|---|---|
| A, from Example 5 | 0.5 | 0.3977 ± 0.03 |

-continued

| Static reducing Agent (SRA) | Weight percent of SRA | Cationic Deposition (mg/g hair) ± S.D. |
|---|---|---|
| | 1.0 | 0.4648 ± 0.04 |
| | 2.0 | 0.5053 ± 0.03 |
| | 3.0 | 0.5097 ± 0.03 |
| B, from Example 5 | 0.5 | 0.4719 ± 0.04 |
| | 1.0 | 0.4018 ± 0.05 |
| | 2.0 | 0.5235 ± 0.02 |
| | 3.0 | 0.4822 ± 0.03 |

The above data demonstrate the beneficial effect of the static-reducing agent in maintaining a substantially similar or reduced amount of cationic deposition on the hair from that produced by the distearyldimethylammonium chloride as demonstrated in Example 2.

EXAMPLE 7. Cationic Deposition on Hair

The procedure of Example 2 was followed except that the aqueous conditioning composition contained 2 weight percent static-reducing agent B from Example 5, 2 weight percent propylene glycol and from 0.5 to 2.0 weight percent distearyldimethylammonium chloride (cationic) as shown below. The amount of cationic deposition was calculated from the panelists' ratings based on the specific cationic color standard for distearyldimethylammonium chloride. The results are shown below.

| Weight percent Cationic in Composition | Cationic Deposition (mg/g hair) ± S.D. |
|---|---|
| 0.5 | 0.4103 ± 0.05 |
| 1.0 | 0.4367 ± 0.04 |
| 1.5 | 0.4905 ± 0.04 |
| 2.0 | 0.4305 ± 0.04 |

The above data show the beneficial effect of the static-reducing agent in maintaining the substantially similar amount of cationic deposition produced by distearyldimethylammonium chloride throughout the range used (as demonstrated in Example 2). The data further indicate that distearyldimethylammonium chloride did not exhaust from the composition nor did it cause increased cationic deposition with increasing concentration in combination with the static-reducing agent.

EXAMPLE 8. Reduction of Combing-Induced Static Charge in Hair

This example demonstrates the synergistic effect of the static-reducing agent and the cationic polymer used together in weight proportions of from 5:1 to 20:1.

The conditioner composition E of Example 1 was utilized for this study, except for the ultraviolet absorber and polyoxypropylene (30) cetyl ether, absent to eliminate a possible emollient effect that may be provided by that latter material. Variable amounts of caprylic/capric triglyceride as static-reducing agent and quaternary nitrogen-containing polymers were included as is shown hereinafter. It is noted that 2 weight percent distearyldimethylammonium chloride was present in each composition.

A series of normal natural brown tresses (DeMeo Brothers, New York) about 6 inches in length and about 2 grams in weight were shampooed with a conventional shampoo known to have no static-reducing agents present. The shampooed tresses were individually conditioned with 0.5 gram of one of the conditioner compositions prepared. The conditioner was applied to the wet hair tress and allowed to contact the hair fibers for one minute. The tress was then rinsed with water having a temperature of about 38 degrees C. (about 100 degrees F.) for about 30 seconds.

Each conditioned tress was placed in a dessicator chamber to dry overnight at a relative humidity of 20% and at ambient, room temperature. The dry tress was subsequently combed 50 times at 84 strokes of the comb per minute using a hard rubber comb attached to an automated combing device. The electric field strength of the combing-induced static charge on the hair was measured in kilovolts per meter (kv/m) with a Keithly Static Meter.

A second series of tresses were similarly prepared except that, prior to treating the hair in the manner described above, the tresses were given one bleaching with a commercial bleach product followed by one permanent wave with a commercial salon wave product, according to each manufacturer's instructions. This series of tresses are identified hereinafter as bleached-waved hair.

The proportions of static-reducing agent (SRA) and cationic polymer (CP) present in the conditioner compositions used, and the results obtained follow.

| | | Combing-Induced Static Charge on Hair (Kilovolts/m) | |
|---|---|---|---|
| Composition | Weight Ratio* (SRA:CP) | Normal Hair Series | Bleached-Waved Hair Series |
| A | 0.0:0.0 | 1.9 | 1.7 |
| B | 2:0.0 | 1.9 | 1.2 |
| C | 0.0:0.2 | 2.1 | 2.2 |
| D | 1:0.2 | 1.5 | 1.8 |
| E | 2:0.2 | 1.6 | 1.5 |
| F | 3:0.2 | 1.6 | 1.4 |
| G | 4:0.2 | 2.1 | 1.5 |

*The weight ratio of SRA:CP in formulae D, E, F, and G respectively represent weight ratios of 5:1, 10:1, 15:1 and 20:1.

The data show that the static-reducing agent and the cationic polymer individually induced more static charge on the dry hair when it was combed than did the combination of the two. The data also show that the combination of static-reducing agent and cationic polymer had a synergistic effect in decreasing the combing-induced static charge on the hair.

The present invention has been described with respect to preferred embodiments. It will be clear to those skilled in the art that modifications and/or variations of the disclosed compositions and methods can be made without departing from the scope of the invention set forth herein.

What is claimed is:

1. A human hair conditioner consisting essentially of an aqueous composition containing about 0.25 to about 4 weight percent of a static-reducing agent comprised of a nonionic, water-insoluble, non-oily organic material having a Brookfield viscosity at 26° C. of less than about 50 centipoises, that is a liquid at 20° C. and has a refractive index at 25° C. of about 1.4 to about 1.5, about 0.05 to about 1.0 weight percent of a cationic, film-forming polymer containing a plurality of quaternary nitrogen atoms, and about 0.25 to about 4 weight percent of a distearyldimethylammonium salt, the weight ratio of said static-reducing agent to said cationic polymer being about 2:1 to about 20:1.

2. The conditioner according to claim 1 wherein said static-reducing agent is caprylic/capric triglyceride or $C_{12}$-$C_{15}$ alcohols benzoate.

3. The conditioner according to claim 1 wherein said static-reducing agent is present at about 1.5 to about 2.5 weight percent of said composition.

4. The conditioner according to claim 1 wherein said cationic polymer is selected from the group consisting of
   (a) a polymeric quaternary ammonium salt reaction product of hydroxyethyl cellulose reacted with a trimethylammonium-substituted epoxide;
   (b) a copolymer of hydroxyethyl cellulose and diallyldimethylammonium chloride;
   (c) a homopolymer of diallyldimethylammonium chloride;
   (d) a polymer reaction product of diallyldimethylammonium chloride and acrylamide monomers;
   (e) a quaternary ammonium polymer reaction product of dimethyl sulfate and copolymer of vinyl pyrrolidone and dimethylaminoethyl methacrylate;
   (f) a copolymer reaction product of acrylamide and methacryloyl-oxyethyl trimethylammonium chloride; and
   (g) a copolymer reaction product of methyl-vinylimidazolium chloride and vinyl pyrrolidone.

5. The conditioner according to claim 1 wherein said cationic polymer is present at about 0.1 to about 0.5 weight percent of said composition.

6. The conditioner according to claim 1 wherein said distearyldimethylammonium salt is distearyldimethylammonium choride.

7. The conditioner according to claim 1 wherein said distearyldimethylammonium salt is present at about 0.5 to about 2 weight percent of said composition.

8. The conditioner according to claim 1 wherein said weight ratio of said static-reducing agent to said cationic polymer is about 5:1 to about 20:1.

9. The conditioner according to claim 1 wherein said aqueous composition is a stable emulsion.

10. A human hair conditioner consisting essentially of an aqueous emulsion having dispersed therein a static-reducing agent of caprylic/capric triglyceride or $C_{12}$-$C_{15}$ alcohols benzoate present in an amount of about 1.5 to about 2.5 weight percent, a cationic, film-forming polymer containing a plurality of quaternary nitrogen atoms that is a reaction product of hydroxyethyl cellulose reacted with a trimethylammonium-substituted epoxide present in an amount of about 0.1 to about 0.5 weight percent, and about 0.5 to about 2 weight percent distearyldimethylammonium chloride, the weight ratio of said static-reducing agent to said cationic polymer being about 5:1 to about 20:1.

11. A method of conditioning human hair in the presence of a hair set-improving cationic polymer to provide a reduced amount of combing-induced static charge when the conditioned hair in the dry state is combed comprising the steps of:
   providing a human hair conditioner consisting essentially of an aqueous composition of about 0.25 to about 4 weight percent static-reducing agent comprised of a nonionic, water-insoluble, non-oily organic material having a Brookfield viscosity at 26° C. of less than about 50 centipoises that is a liquid at 20° C. and has a refractive index at 25° C. of about 1.4 to about 1.5, about 0.05 to about 1.0 weight percent of a cationic, film-forming polymer containing a plurality of quaternary nitrogen atoms, and about 0.25 to about 4 weight percent of a distearyldimethylammonium salt, the weight ratio of said static-reducing agent to said quaternary nitrogen-containing polymer being about 2:1 to about 20:1;
   applying said conditioner in a substantially homogeneous form to human hair;
   maintaining said application for a time period sufficient for said conditioner to contact the hair fibers;
   rinsing the contacted hair fibers with water; and
   drying the water-rinsed hair.

12. The method according to claim 11 wherein said static-reducing agent is caprylic/capric triglyceride or $C_{12}$-$C_{15}$ alchols benzoate.

13. The method according to claim 11 wherein said cationic polymer is selected from the group consisting of
   (a) a polymeric quaternary ammonium salt reaction product of hydroxyethyl cellulose reacted with a trimethylammonium-substituted epoxide;
   (b) a copolymer of hydroxyethyl cellulose and diallyldimethylammonium chloride;
   (c) a homopolymer of diallyldimethylammonium chloride;
   (d) a polymer reaction product of diallyldimethylammonium chloride and acrylamide monomers;
   (e) a quaternary ammonium polymer reaction product of dimethyl sulfate and copolymer of vinyl pyrrolidone and dimethylaminoethyl methacrylate;
   (f) a copolymer reaction product of acrylamide and methacryloyl-oxyethyl trimethylammonium chloride; and
   (g) a copolymer reaction product of methyl-vinylimidazolium chloride and vinyl pyrrolidone.

14. The method according to claim 11 wherein said distearyldimethylammonium salt is distearyldimethylammonium choride and is present at about 0.5 to about 2 weight percent of said composition.

15. The method according to claim 11 wherein said aqueous composition is a stable emulsion.

* * * * *